United States Patent [19]

Dobrusskin et al.

[11] 4,155,025
[45] May 15, 1979

[54] HIGH-PRESSURE MERCURY-VAPOR DISCHARGE ULTRAVIOLET RADIANT ENERGY LAMP

[75] Inventors: Alexander Dobrusskin, Taufkirchen; Günter Schmid, Munich, both of Fed. Rep. of Germany

[73] Assignee: Patent-Treuhand-Gesellschaft, Munich, Fed. Rep. of Germany

[21] Appl. No.: 899,521

[22] Filed: Apr. 24, 1978

[30] Foreign Application Priority Data

Apr. 27, 1977 [DE] Fed. Rep. of Germany ....... 2718735

[51] Int. Cl.² .......................................... H01J 61/18
[52] U.S. Cl. .................................... 313/229; 313/225
[58] Field of Search ................................ 313/229, 225

[56] References Cited

U.S. PATENT DOCUMENTS 3,590,307  6/1971  Dobrusskin et al. ............ 313/229 X

FOREIGN PATENT DOCUMENTS 1290189  9/1972  United Kingdom.

OTHER PUBLICATIONS

Reiling, "Journal of the Optical Society of America", (1964), vol. 54, No. 4, pp. 532–540.

Primary Examiner—Gerard R. Strecker
Assistant Examiner—Darwin R. Hostetter
Attorney, Agent, or Firm—Flynn & Frishauf

[57] ABSTRACT

A high-pressure mercury-vapor discharge lamp having a fill which comprises a combination of any two or more elements selected from iron, nickel, and cobalt. The lamp is a strong ultraviolet radiator particularly having the radiation in the UV range of between about 310 and 350 nm substantially enhanced. The lamps are useful in industry particularly as a UV source in the graphic arts field, and for a strong source of ultraviolet radiation for humans, particularly radiation in the aforenoted range of wavelengths.

11 Claims, 2 Drawing Figures

HIGH-PRESSURE MERCURY-VAPOR DISCHARGE ULTRAVIOLET RADIANT ENERGY LAMP

BACKGROUND OF THE INVENTION

The invention provides high-pressure mercury-vapor discharge lamps having a high output of ultraviolet radiation. When compared with lamps of the type used for general lighting service, the proportion of medium-wave and long-wave ultraviolet radiation, relative to the total radiation output of the lamp, is high for the lamps in the present invention. The said proportion of UV radiation is able to deeply penetrate skin and is therefore useful for therapeutic radiation purposes. The UV radiation is also useful for causing photocatalytic and photochemical reactions.

Because almost all UV effects having a biological utility may be obtained with lamps of the high-pressure mercury-vapor discharge type, such discharge type of lamp is used in most of the conventional lamp structures used as UV radiators.

British patent specification No. 1,290,189 and U.S. Pat. No. 3,590,307 disclose that when using a high-pressure mercury-vapor discharge which also contains iron and/or manganese halide, and optionally tin halide, it is possible to increase the total output of ultraviolet radiation relative to the power input of the radiator and further to increase the relative ratio of long-wave UV-radiation (in the range of wavelengths from 315 to 380 nm (UV-A)) to medium-wave UV-radiation (in the range of wavelengths from 280 to 315 nm (UV-B)). U.S. Pat. No. 3,416,023 discloses a high-pressure mercury-vapor discharge lamp used for irradiation purposes which as a result of the inclusion of cobalt chloride in the fill, emits only long-wave UV and short-wave visible light. Quite generally, the use of, e.g., iron iodide or cobalt iodide or nickel iodide, respectively, in high-pressure mercury-vapor discharge lamps for general lighting service has become known from the article in the "Journal of the Optical Society of America" (1964), Vol. 54, No. 4, pages 532–540, which reports studies directed to the determination of those metal halide additives to the mercury by which highest luminous efficacy and good color rendering of the lamps are obtainable, i.e., the most favorable characteristics of the lamps in the visual spectral range. No reference is had in said paper, however, to the characteristics of the elements iron, nickel, cobalt in the ultraviolet spectral range. U.S. Pat. No. 4,074,164 discloses sunlamps which contain an iron halide in the fill which also contains at least some of mercury, rare earth, and tin halides.

It is an object of the present invention to provide a radiation source of increased integral output in the range of wavelengths from 300 to 400 nm compared with known devices, and particularly wherein the proportion of radiation in the border range between medium-wave and long-wave ultraviolet radiation (310–350 nm) is high.

THE INVENTION

The present invention provides high-pressure mercury-vapor discharge lamps having a fill which contains an inert gas as the starting gas. The fill also contains (i) nickel and/or (iron plus cobalt), (ii) iron plus nickel, or (iii) nickel plus cobalt. The total amount of said nickel, iron and/or cobalt (at least two of which must be present or nickel alone) when calculated as the metal is between about 0.01 and 1 mgr/cc, preferably 0.06 and 0.6 mgr/cc of fill. The fill also preferably contains an approximately equivalent amount of halogen to form the halides of said metals. It is preferred that the amount of iron should not exceed 50% by weight of the additive. This is particularly useful since the total amount of additive introduced into the lamp is limited so as to observe the electrical characteristics of the radiation. Nonetheless the lamps of the present invention have the advantage that they may contain as large an amount as possible of metals which result in radiation emitted in the range of wavelengths between 310 and 350 nm.

When using iodine and/or bromine as the halogen of the lamp fill, it is suitably added in combination with mercury, for example in the form of $HgI_2$ or $HgBr_2$, respectively. Although the amount of halogen is preferably equivalent to the metal additive in the fill other than mercury, the use of an excess or an amount smaller than the equivalent amount, is also within the scope of the present invention.

The present invention is further illustrated in the subject matter of the drawings and the following examples wherein.

Figure 1:
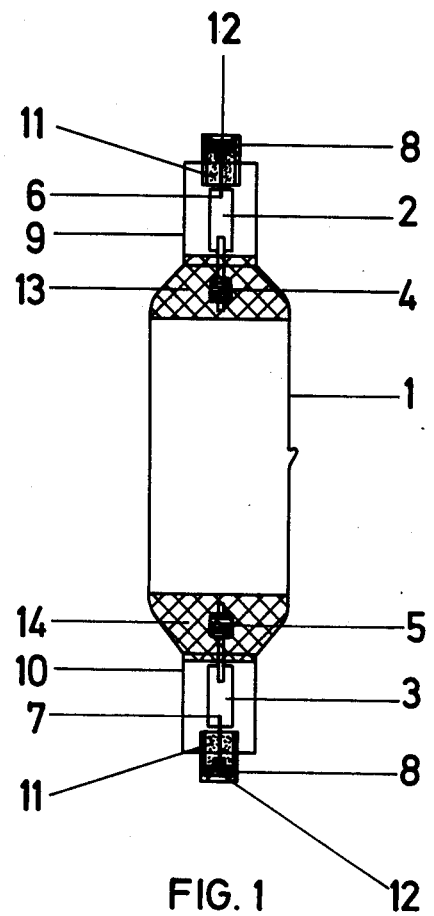
FIG. 1 is a sectional view of a double ended lamp.

With reference to FIG. 1, the discharge tube 1 is usually made of quartz glass. For fields of application of the lamp in which the proportion of short-wave UV-radiation is not wanted, the quartz glass is doped with $TiO_2$ or $VO_2$ or the like, or provided with a coating of these oxides. A vacuum-tight foil conductive seal 2, 3 is provided at each end of the discharge tube 1, connecting the mandrel wires of the tungsten electrodes 4, 5 (which are activated with $ThO_2$) and the lead-in wires 6, 7. A ceramic cylinder 8 with indentations is used as the base which is positioned with part of its length (up to the end of the indentations) onto the respective end seal 9, 10 and secured in position by cement 11. Internally of the cylindrical base 8 is a contact 12 to which the lead-in wire 6, 7 is connected. In order to obtain uniform temperature distribution, the ends of the tube 1 may be provided with a heat accumulating coating 13, 14 of $ZrO_2$. The discharge tube 1 has an inner diameter of 16 mm; the electrode spacing is 44 mm; and the fill volume is about 11 cc. The lamp has a power input of 360 W and is operated with 3.5 A from 220 V A.C. voltage. The following table reports the fill quantities of three lamps of the present invention.

| Example No. | Co (mgr.) | Ni (mgr.) | Fe (mgr.) | $HgI_2$ (mgr.) | Hg (mgr.) | Ar (torr) |
|---|---|---|---|---|---|---|
| 1 | 0.5 | 0.5 | — | 7.7 | 14 | 30 |
| 2 | 0.6 | 0.2 | 0.2 | 7.7 | 14 | 30 |
| 3 | 0.6 | — | 0.4 | 7.7 | 14 | 30 |

With nickel and iron or with nickel alone good results are also obtained.

Figure 2:
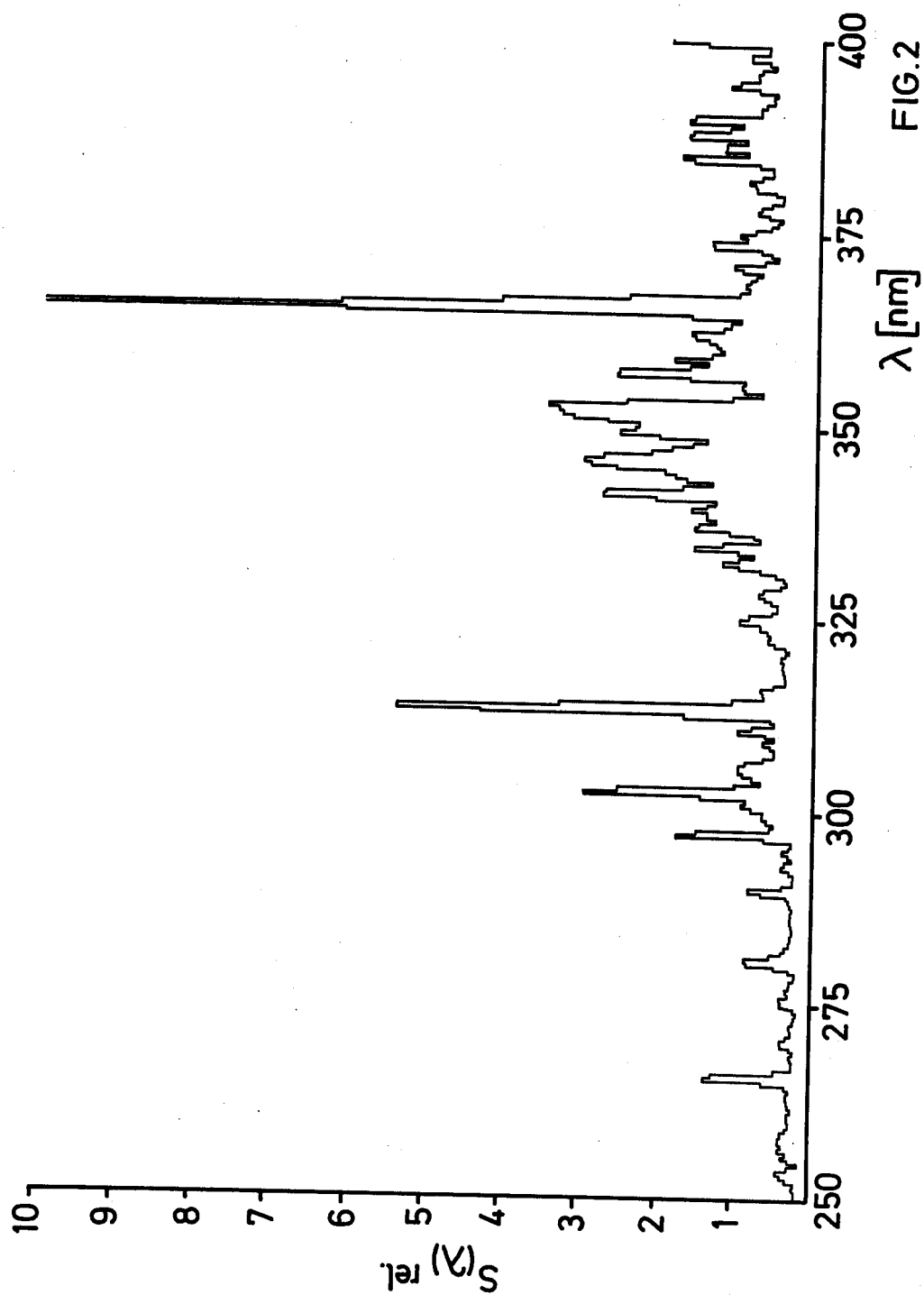
FIG. 2 is a reproduction of the spectral radiant intensity distribution $S_{(\lambda)}$ of the lamp of the present invention.

The spectral radiation intensity distribution of the radiation from the lamp containing the fill of Example 2 which is the preferred embodiment of the invention, is reproduced in FIG. 2. From this data, it is evident that the radiant emission of the entire UV range corresponds to more than 20% of the electrical power input to the lamp. The UV radiation having a wavelength in the range of between about 310 and 350 nm, which is particularly effective in therapeutic and cosmetic applications, corresponds to about 6% of the input power to the lamp. This establishes that the proportion of UV in this range is doubled when compared with the corresponding radiation from a lamp which contains only iron halide as the additive instead of the combination of metal halides of the present invention.

The lamps of the present invention are of importance for therapeutic purposes, especially for use in the medical treatment of dermatoses, such as psoriasis. The medical treatment with ultraviolet radiation is particularly effective when there is provided, in addition to a high proportion of long-wave UV (UV-A), a noticeable proportion of radiation in the border range between medium-wave (UV-B) and long-wave (UV-A), namely, from 310 to 350 nm. Due to the high proportions of UV-A and UV-B radiation, the duration of medical treatment is considerably reduced. The lamps of the present invention which provide high integral UV-output in the range of wavelengths from about 300 to about 400 nm are also preferred UV radiation sources in other fields, such as pressure drying, applying backing to foil, UV-curing of plastics, printed circuit board fabrication, and as a light source in the graphics industry.

Various changes and modifications may be made within the scope of the inventive concept.

High-pressure mercury-vapor discharge lamps of the type of which the present application is an improvement are disclosed in U.S. Pat. No. 3,590,307.

We claim:

1. A high-pressure mercury-vapor discharge ultraviolet radiant energy lamp comprising a radiation source mounted within an ultraviolet transmissive envelope, said envelope containing the halogen vapor discharge fill comprising mercury and at least one combination of any two or more iron group elements selected from the group consisting of iron, nickel and cobalt, the total amount of said iron group elements being from about 0.01 to 1 mgr/cc of fill, said lamp having ultraviolet radiant energy output in the range of from about 310 to 350 nm corresponding to about 6% of the power input to said lamp.

2. The lamp of claim 1 wherein said combination of iron group elements consists of nickel and cobalt.

3. The lamp of claim 1 wherein said combination of iron group elements consists of iron and cobalt.

4. The lamp of claim 1 wherein said combination of iron group elements consists of nickel and iron.

5. The lamp of claim 1 wherein said combination of iron group elements consists of nickel, cobalt and iron.

6. The lamp of claim 1 wherein said combination of iron group elements includes iron as one of the iron group elements in an amount not in excess of 50% by weight of the total weight of said combination of iron group elements.

7. The lamp according to any of claims 1 through 6 containing an amount of halogen substantially equivalent to the stoichiometric amount for the formation of the halides of said metals.

8. The lamp of claim 7 wherein the halogen is selected from the group consisting of iodine and bromine, and said halogen is introduced into the fill in the form of at least one halide selected from the group consisting of $HgI_2$ and $HgBr_2$.

9. The lamp of claim 8 wherein said fill also contains argon as a starter gas.

10. The lamp of claim 1 wherein said fill also contains an inert starter gas.

11. The lamp of claim 1 wherein the total amount of said iron group elements is from about 0.06 to 0.6 mgr/cc of fill.

* * * * *